(12) United States Patent
Gulati (10) Patent No.: US 7,047,136 B2
(45) Date of Patent: *May 16, 2006

(54) INTERFEROMETRIC TECHNIQUE FOR QUANTITATING BIOLOGICAL INDICATORS

(75) Inventor: Sandeep Gulati, La Canada Flintridge, CA (US)

(73) Assignee: ViaLogy Corp., Altadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/677,403

(22) Filed: Oct. 1, 2003

(65) Prior Publication Data

US 2004/0072232 A1    Apr. 15, 2004

Related U.S. Application Data

(63) Continuation of application No. 10/189,885, filed on Jul. 2, 2002, now Pat. No. 6,704,662, which is a continuation of application No. 09/523,539, filed on Mar. 10, 2000, now abandoned, which is a continuation of application No. 09/253,791, filed on Feb. 22, 1999, now Pat. No. 6,245,511.

(51) Int. Cl.
   G01N 33/50   (2006.01)
   G01N 33/48   (2006.01)

(52) U.S. Cl. .......................... 702/19; 702/20; 702/27; 435/6; 435/91.1; 435/91.2; 706/45; 706/47

(58) Field of Classification Search .................. 435/6, 435/91.1, 91.2; 702/19, 27; 706/45, 47; 712/200

See application file for complete search history.

(56) References Cited

U.S. PATENT DOCUMENTS

| | | | | |
|---|---|---|---|---|
| 4,686,695 A | * | 8/1987 | Macovski | 378/146 |
| 5,236,826 A | * | 8/1993 | Marshall | 435/7.92 |
| 5,784,162 A |   | 7/1998 | Cabib et al. | |
| 5,817,462 A | * | 10/1998 | Garini et al. | 435/6 |
| 6,136,541 A | * | 10/2000 | Gulati | 435/6 |
| 6,142,681 A |   | 11/2000 | Gulati | |
| 6,671,625 B1 | * | 12/2003 | Gulati | 702/20 |
| 6,780,589 B1 | * | 8/2004 | Gulati | 435/6 |
| 2004/0111219 A1 | * | 6/2004 | Gulati | 702/19 |

* cited by examiner

Primary Examiner—Michael Borin
(74) Attorney, Agent, or Firm—Fish & Richardson P.C.

(57) ABSTRACT

A technique is described for quantitating biological indicators, such as viral load, using interferometric interactions such as quantum resonance interferometry. A diffusion curve for the biological indicator of interest is generated from at least two measurements from a patient sample. In some embodiments, the patient samples are in the form of a microarray output pattern to which the patient sample has been applied. After the diffusion curve has been generated, subsequent patient samples are mapped to the diffusion curve to provide a quantitative measure of the biological indicator of interest.

19 Claims, 5 Drawing Sheets

```
           FRACTAL
          FILTERING
              │
              ▼
   ┌──────────────────────┐ ─ 302
   │  GENERATE PARTITIONED │
   │ ITERATED FRACTAL SYSTEM (IFS) │
   │  MODEL REPRESENTATIVE OF │
   │    THE DOT SPECTROGRAM │
   └──────────────────────┘
              │
              ▼
   ┌──────────────────────┐ ─ 304
   │  DETERMINE AFFINE     │
   │  PARAMETERS FOR THE   │
   │      IFS MODEL        │
   └──────────────────────┘
              │
              ▼
   ┌──────────────────────┐ ─ 306
   │ MAP THE DOT SPECTROGRAM │
   │ ONTO THE VIRAL DIFFUSION │
   │  CURVE USING THE IFS  │
   └──────────────────────┘
```

INTERFEROMETRIC TECHNIQUE FOR QUANTITATING BIOLOGICAL INDICATORS

This application is a Continuation of U.S. patent application Ser. No. 10/189,885, now U.S. Pat. No. 6,704,662, entitled "Technique for Quantitating Biological Markers Using Quantum Resonance Interferometry" which is a Continuation of U.S. patent application Ser. No. 09/523,539 entitled "Method and System for Quantitation of Viral Load Using Microarrays" filed Mar. 10, 2000, now abandoned, which is a Continuation of U.S. patent application Ser. No. 09/253,791, now U.S. Pat. No. 6,245,511, entitled "Method and Apparatus for Exponentially Convergent Therapy Effectiveness Monitoring Using DNA Microarray Based Viral Load Measurements" filed Feb. 22, 1999, all of which are hereby incorporated by reference.

FIELD OF THE INVENTION

The invention generally relates to techniques for monitoring the effectiveness of medical therapies and dosage formulations, and in particular to techniques for monitoring therapy effectiveness using viral load measurements.

BACKGROUND OF THE INVENTION

It is often desirable to determine the effectiveness of therapies, such as those directed against viral infections, including therapies involving individual drugs, combinations of drugs, or other related therapies. One conventional technique for monitoring the effectiveness of a viral infection therapy is to measure and track a viral load associated with the viral infection, wherein the viral load is a measurement of a number of copies of the virus within a given quantity of blood, such per milliliter of blood. The therapy is deemed effective if the viral load is decreased as a result of the therapy. A determination of whether any particular therapy is effective is helpful in determining the appropriate therapy for a particular patient and also for determining whether a particular therapy is effective for an entire class of patients. The latter is typically necessary in order to obtain FDA approval of any new drug or medical device therapy. Viral load monitoring is also useful for research purposes such as for assessing the effectiveness of new antiviral compounds determine, for example, whether it is useful to continue developing particular antiviral compounds or to attempt to gain FDA market approval.

A test to determine the viral load can be done with blood drawn from T-cells or from other standard sources. The viral load is typically reported either as an absolute number, i.e., the number of virus particles per milliliter of blood or on a logarithmic scale. Likewise, decreases in viral load are reported in absolute numbers, logarithmic scales, or as percentages.

It should be noted though that a viral load captures only a fraction of the total virus in the body of the patient, i.e., it tracks only the quantity of circulating virus. However, viral load is an important clinical marker because the quantity of circulating virus is the most important factor in determining disease outcome, as changes in the viral load occur prior to changes in other detectable factors, such as CD4 levels. Indeed, a measurement of the viral load is rapidly becoming the acceptable method for predicting clinical progression of certain diseases such as HIV.

Insofar as HIV is concerned, HIV-progression studies have indicated a significant correlation between the risk of acquiring AIDS and an initial HIV baseline viral load level. In addition to predicting the risk of disease progression, viral load testing is useful in predicting the risk of transmission. In this regard, infected individuals with higher viral load are more likely to transmit the virus than others.

Currently, there are several different systems for monitoring viral load including quantitive polymerase chain reaction (PCR) and nucleic acid hybridization. Herein, the term viral load refers to any virological measurement using RNA, DNA, or p24 antigen in plasma. Note that viral RNA is a more sensitive marker than p24 antigen. p24 antigen has been shown to be detectable in less than 50% asymptomatic individuals. Moreover, levels of viral RNA rise and fall more rapidly than levels of CD4+ lymphocytes. Hence, changes in infection can be detected more quickly using viral load studies based upon viral RNA than using CD4 studies. Moreover, viral load values have to date proven to be an earlier and better predictor of long term patient outcome than CD4-cell counts. Thus, viral load determinations are rapidly becoming an important decision aid for anti-retro viral therapy and disease management. Viral load studies, however, have not yet completely replaced CD+ analysis in part because viral load only monitors the progress of the virus during infection whereas CD4+ analysis monitors the immune system directly. Nevertheless, even where CD4+ analysis is effective, viral load measurements can supplement information provided by the CD4 counts. For example, an individual undergoing long term treatment may appear stable based upon the observation of clinical parameters and CD4 counts. However, the viral load of the patient may nevertheless be increasing. Hence, a measurement of the viral load can potentially assist a physician in determining whether to change therapy despite the appearance of long term stability based upon CD4 counts.

Thus, viral load measurements are very useful. However, there remains considerable room for improvement. One problem with current viral load measurements is that the threshold level for detection, i.e., the nadir of detection, is about 400–500 copies per milliliter. Hence, currently, if the viral load is below 400–500 copies per milliliter, the virus is undetectable. The virus may nevertheless remain within the body. Indeed, considerable quantities of the virus may remain within the lymph system. Accordingly, it would be desirable to provide an improved method for measuring viral load which permits viral load levels of less than 400–500 copies per milliliter to be reliably detected.

Another problem with current viral load measurement techniques is that the techniques are typically only effective for detecting exponential changes in viral loads. In other words, current techniques will only reliably detect circumstances wherein the viral load increases or decreases by an order of magnitude, such by a factor of 10. In other cases, viral load measurements only detect a difference between undetectable levels of the virus and detectable levels of the virus. As can be appreciated, it would be highly desirable to provide an improved method for tracking changes in viral load which does not require an exponential change in the viral load for detection or which does not require a change from an undetectable level to a detectable level. Indeed, with current techniques, an exponential or sub-exponential change in the viral load results only in a linear change in the parameters used to measure the viral load. It would instead be highly desirable to provide a method for monitoring the viral load which converts a linear change in the viral load into an exponential change within the parameters being measured to thereby permit very slight variations in viral load to be reliably detected. In other words, current viral load detection techniques are useful only as a qualitative estimator, rather than as a quantative estimator.

One reason that current viral load measurements do not reliably track small scale fluctuations in the actual number of viruses is that a significant uncertainty in the measurements often occurs. As a result, individual viral load measurements have little statistical significance and a relatively large number of measurements must be made before any statistically significant conclusions can be drawn. As can be appreciated it would be desirable to provide a viral load detection technique which can reliably measure the viral load such that the statistical error associated with a single viral load measurement is relatively low to permit individual viral load measurements to be more effectively exploited.

Moreover, because individual viral load measurements are not particularly significant when using current methods, treatment decisions for individual patients based upon the viral load measurements must be based only upon long term changes or trends in the viral load resulting in a delay in any decision to change therapy. It would be highly desirable to provide an improved method for measuring and tracking viral load such that treatment decisions can be made much more quickly based upon short term trends of measured viral load.

As noted above, the current nadir of viral load detectability is at 400–500 copies of the virus per milliliter. Anything below that level is deemed to be undetectable. Currently the most successful and potent multi-drug therapies are able to suppress viral load below that level of detection in about 80–90 percent of patients. Thereafter, viral load is no longer an effective indicator of therapy. By providing a viral load monitoring technique which reduces the nadir of detectability significantly, the relative effectiveness of different multi-drug therapies can be more effectively compared. Indeed, new FDA guidelines for providing accelerated approval of a new drug containing regimen requires that the regimen suppress the viral load below the current nadir of detection in about 80 to 85 percent of cases. If the new regimen suppresses the viral load to undetectable levels in less than 80 to 85 percent of the cases, the new drug will gain accelerated approval only if it has other redeeming qualities such as a preferable dosing regimen (such as only once or twice per day), a favorable side effect profile, or a favorable resistance or cross-resistance profile. Thus, the ability of a regimen to suppress the viral load below the level of detection is an important factor in FDA approval. However, because the level of detectability remains relatively high, full approval is currently not granted by the FDA solely based upon the ability of the regimen to suppress the viral load below the minimum level of detection. Rather, for full approval, the FDA may require a further demonstration of the durability of the regimen, i.e., a demonstration that the drug regimen suppresses the viral load below the level of detectability and keeps it below the level of detectability for some period of time.

As can be appreciated, if a new viral load measurement and tracking technique were developed which could reliably detect viral load at levels much lower than the current nadir of detectability, the FDA may be able, using the new technique, to much more precisely determine the effectiveness of a drug regimen for the purposes of granting approval such that a demonstration of the redeeming evalities will no longer be necessary.

For all of these reasons, it would be highly desirable to provide an improved technique for measuring and tracking viral load capable of providing much more precise and reliable estimates of the viral load and in particular capable of reducing the nadir of detectability significantly. The present invention is directed to this end.

SUMMARY OF THE INVENTION

In accordance with a first aspect of the invention, a method is provided for determining the effectiveness of a therapy, such as an anti-viral therapy, by analyzing biochip output patterns generated from biological samples taken at different sampling times from a patient undergoing the therapy. In accordance with the method, a viral diffusion curve associated with a therapy of interest is generated and each of the output patterns representative of hybridization activity is then mapped to coordinates on the viral diffusion curve using fractal filtering. A degree of convergence between the mapped coordinates on the viral diffusion curve is determined. Then, a determination is made as to whether the therapy of interest has been effective based upon the degree of convergence.

In an exemplary embodiment, the viral diffusion curve is spatially parameterized such that samples map to coordinates near the curve maxima, if the viral load is increasing (i.e., therapy or dosage is ineffective). In this manner, any correlation between rate and extent of convergence across different patient samples is exploited to provide a quantitative and qualitative estimate of therapy effectiveness.

Also in the exemplary embodiment, the biological sample is a DNA sample. The output pattern of the biochip is quantized as a dot spectrogram. The viral diffusion curve is generated by inputting parameters representative of viral load studies for the therapy of interest, generating a preliminary viral diffusion curve based upon the viral load studies; and then calibrating a degree of directional causality in the preliminary viral diffusion curve to yield the viral diffusion curve. The parameters representative of the viral load studies include one or more of baseline viral load (BVL) set point measurements at which detection is achieved, BVL at which therapy is recommended and viral load markers at which dosage therapy is recommended. The step of generating the preliminary viral diffusion curve is performed by selecting a canonical equation representative of the viral diffusion curve, determining expectation and mean response parameters for use in parameterizing the equation selected to represent the viral diffusion curve and parameterizing the equation selected to represent the viral diffusion curve to yield the preliminary viral diffusion curve.

Also, in the exemplary embodiment, each dot spectrogram is mapped to the viral diffusion curve using fractal filtering by generating a partitioned iterated fractal system IFS model representative of the dot spectrogram, determining affine parameters for IFS model, and then mapping the dot spectrogram onto the viral diffusion curve using the IFS. Before the dot spectrograms is mapped to the viral diffusion curve, the dot spectrograms are interferometrically enhanced. After the mapping, any uncertainty in the mapped coordinates is compensated for using non-linear information filtering.

In accordance with a second aspect of the invention, a method is provided for determining the viral load within a biological sample by analyzing an output pattern of a biochip to which the sample is applied. In accordance with the method, a viral diffusion curve associated with a therapy of interest is generated and then calibrated using at least two viral load measurements. Then the output pattern for the sample is mapped to coordinates on the calibrated viral diffusion curve using fractal filtering. The viral load is determined from the calibrated viral diffusion curve by interpreting the coordinates of the viral diffusion curve.

Apparatus embodiments are also provided. By exploiting aspects of the invention, disease management decisions related to disease progression, therapy and dosage effectiveness may be made by tracking the coordinates on the viral diffusion curve as successive DNA-/RNA-based microarray samples are collected and analyzed.

BRIEF DESCRIPTION OF THE DRAWINGS

The features, objects, and advantages of the present invention will become more apparent from the detailed description set forth below when taken in conjunction with the drawings in which like reference characters identify correspondingly throughout and wherein.

DETAILED DESCRIPTION OF EXEMPLARY EMBODIMENTS

With reference to the figures, exemplary method embodiments of invention will now be described. The exemplary method will be described primarily with respect to the determination of changes in viral loads based upon the output patterns of a hybridized biochip microarray using DNA samples, but principles of the invention may be applied to other protein-based samples or to other types of output patterns as well.

Figure 1:
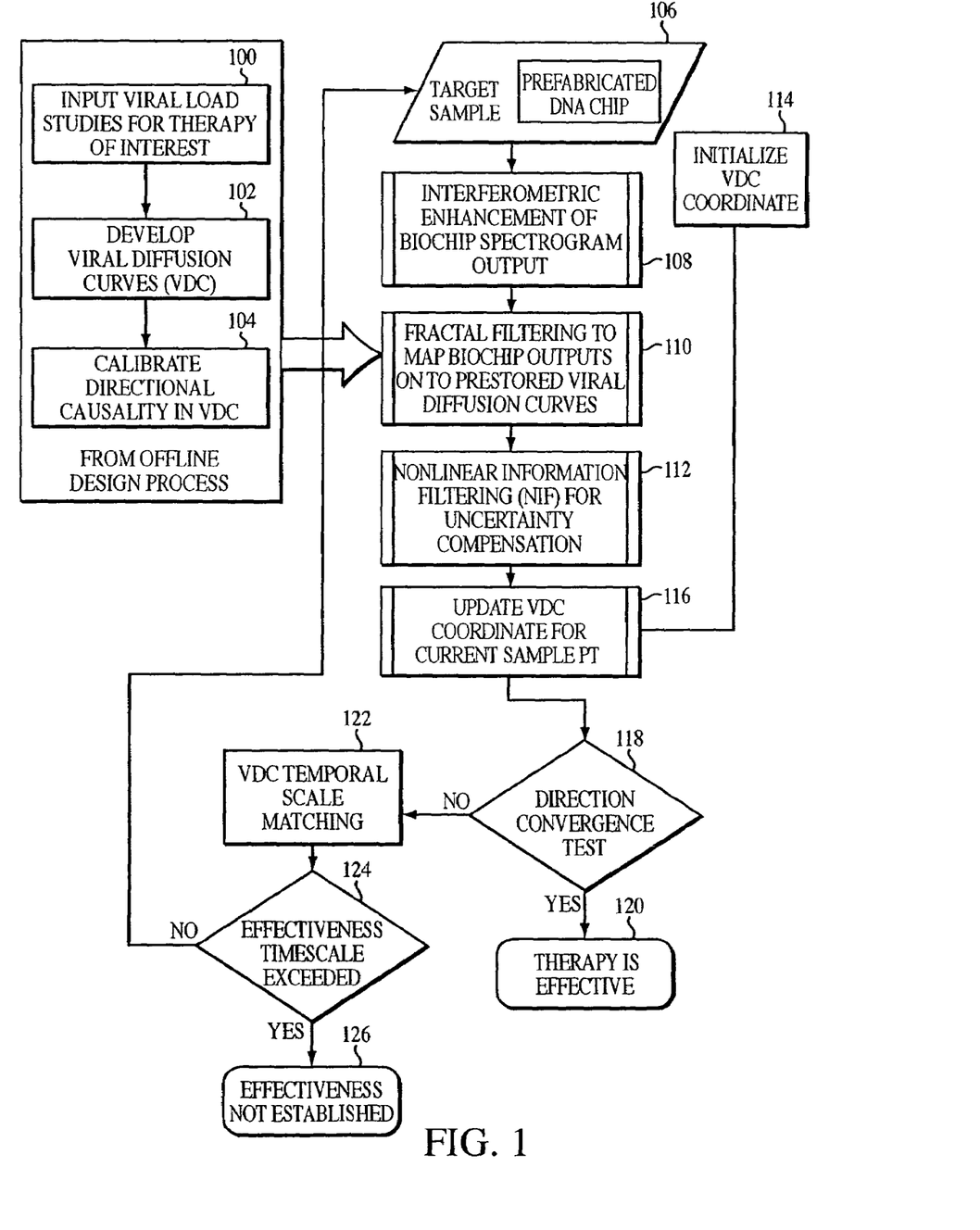
FIG. 1 is a flow chart illustrating an exemplary method for determining the effectiveness of a viral therapy in accordance with the invention.

With reference to FIG. 1, steps will be described for generating viral diffusion curves for use is processing DNA biomicroarray output patterns to determine the effectiveness of therapies imposed upon a patient providing samples for which the outputs are generated. Then, steps will be described for processing the specific output patterns using the VDC's.

An underlying clinical hypothesis of the exemplary method is that antiviral treatment should inhibit viral replication and lower an individual's viral load from baseline or suppress rising values. A stationary or rising viral load after the introduction of antiviral therapy indicates a lack of response to the drug(s) or the development of drug resistance. The VDC exploits the underlying hypothesis in part by correlating the rate of disease progression to a sample point value such that a change in sample point indicates progression.

The Method

At step 100, parameters representative of viral load studies for the therapy of interest are input. A preliminary viral diffusion curve is generated, at step 102, based upon the viral load studies. The parameters representative of the viral load studies include baseline viral load (BVL) set point measurements at which detection is achieved, BVL at which therapy is recommended and viral load markers at which dosage therapy is recommended. At step 104, a degree of directional causality in the preliminary viral diffusion curve is calibrated to yield the final viral diffusion curve.

Steps 100–104 are performed off-line for setting up the VDC's. These steps need be performed only once for a given therapy and for a given set of baseline viral load measurements. Thereafter, any number of DNA biomicroarray output patterns may be processed using the VDC's to determine the effectiveness of the therapy. Preferably, VDC's are generated for an entire set of therapies that may be of interest such that, for any new DNA biomicroarray output pattern, the effectiveness of any of the therapies can be quickly determined using the set of VDC's. In general, the aforementioned steps need be repeated only to update the VDC's based upon new and different baseline viral load studies or if new therapies of interest need to be considered.

In the following, steps will be summarized for processing DNA biomicroarray output patterns using the VDC's to determine whether any therapies of interest represented by the VDC's are effective. To determine the effectiveness of therapy at least two samples of DNA to be analyzed are collected from a patient, preferably taken some time apart, and biomicroarray patterns are generated therefrom. In other cases though, the different samples are collected from different patients.

The output patterns for the DNA biomicroarray are referred to herein as dot spectrograms. A dot spectrogram is generated using a DNA biomicroarray for each sample from an N by M DNA biomicroarray. An element of the array is an "oxel": $o(i,j)$. An element of the dot spectrogram is a hixel: $h(i,j)$. The dot spectrogram is represented by cell amplitudes given by $\Phi(i,j)$ for i: 1 to N, and j: 1 to M.

Dot spectrograms are generated from the samples taken at different times using a prefabricated DNA biomicroarray at step 106. The dot spectrograms are interferometrically enhanced at step 108. Each dot spectrogram is then mapped to coordinates on the viral diffusion curves using fractal filtering at step 110. After the mapping, any uncertainty in the mapped coordinates is compensated for at step 112 using non-linear information filtering.

VDC coordinates are initialized at step 114, then updated in accordance with filtered dot spectrograms at step 116. A degree of convergence between the mapped coordinates on the viral diffusion curves is then determined at step 118 and a determination is made as to whether the therapy of interest has been effective. The determination is based upon whether the degree of convergence increases from one DNA sample to another. An increase in degree of convergence is representative of a lack of effectiveness of the therapy of interest. Hence, if the degree of convergence decreases, then execution proceeds to step 120, wherein a signal is output indicating that the therapy is effective. If the degree of convergence increases, then execution proceeds to step 122 wherein VDC temporal scale matching is performed. Then a determination is made at step 124 whether an effectiveness time scale has been exceeded. If exceeded, then a conclusion is drawn that the effectiveness of the viral therapy cannot be established even if more samples are analyzed. If not exceeded, then execution returns to step 106 wherein another sample taken from the same patient at a latter time is analyzed by repeating steps 106 through 118.

Viral Load Studies

Viral load studies for therapies of interest are parameterized at step 100 as follows. The therapy of interest is selected from a predetermined list of therapies for which viral load studies have been performed. Measurements from viral load studies are input for therapy of interest. As noted, the viral load measurements include one or more of Baseline Viral Load (BVL) set point measurements at which detection is achieved; BVL at which therapy is recommended; and VL markers at which dosage change recommended.

Data for the viral load measurements are obtained, for example, from drug qualification studies on a minimum include dosages, viral limits as well as time cycles within which an anti-viral drug is deemed effective. The data is typically qualified with age/weight outliers and patient history. Attribute relevant to this claim is the $\gamma_1$ or $BVL_{LOW}$ which corresponds to the lowest detection limit shown for a therapy to be effective using conventional assays or any other diagnostic means. $BVL_{NP-LOW}$ denotes the lowest threshold at which viral load is achieved using a nucleotide probe. Using interferometric enhancement technique, $BVL_{NP-LOW} \ll BVL_{LOW}$.

Generation of Viral Diffusion Curves

Figure 2:
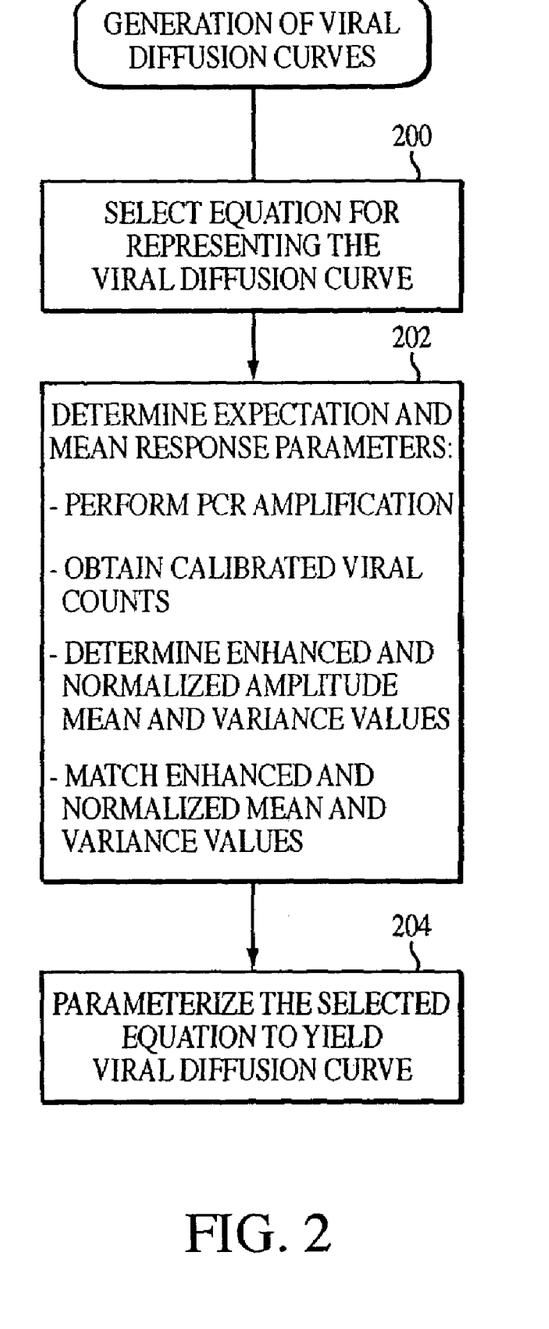
FIG. 2 is a flow chart illustrating an exemplary method for generating Viral Diffusion Curves for use with the method of FIG. 1.

Referring now to FIG. 2, the viral diffusion curves are generated as follows. An equation is selected for representing the VDC at step 200. Expectation ($\mu$) and mean response parameters are determined at step 202 for use in parameterizing the selected equation. Then the equation selected to represent the VDC is parameterized at step 204 to yield a numerical representation of the VDC. These steps will now be described in greater detail.

These steps populate a canonical machine representation, denoted as VDC(i, $\Gamma$, $\gamma$, $\kappa$) (which is a special case of Fokker-Planck equation) to calibrate responses from a viral load detection DNA-array based hybridization biomicroarray.

Expectation and Mean Response Parameters

The expectation ($\mu$) and mean response parameters are then determined at step 202 for use in parameterizing the equation selected to represent the VDC. The expectation and mean response values are determined by: 1) performing conventional PCR amplification; 2) obtaining calibrated viral counts from the PCR amplification; 3) determining enhanced and normalized hybridization amplitude mean and variance values corresponding to the calibrated viral counts; and 4) matching the enhanced and normalized hybridization amplitude mean and variance values.

Two synthetic amplification techniques (in addition to PCR and any designer tagging) are used to achieve VL estimation above the BVL limit set for the exemplary embodiment of the method, namely (a) readout pre-conditioning, and (b) nonlinear interferometric enhancement. Moreover, the expectation match condition implies that:

$$\frac{\text{Expectation } [\text{Log}([\text{interferometrically enhanced image}])]_{\nu[\text{expression set of interest}]}}{\text{Expectation } [\text{preconditioned image amplitude}]_{\nu[\text{expression set of interest}]}} \cong 1$$

i is the index for a diagnostic condition/therapy of interest, $\Gamma$ denotes the parameter vector characterizing the VDC, Variance matching is done similarly with respect to biomicroarray readout. The lower bound of mean response value can be given by:

$$\frac{(\text{Variance } [\text{Log}([\text{interferometrically enhanced image}])]_{\nu[\text{expression set of interest}]}}{\text{Variance } [\text{preconditioned image amplitude}]_{\nu[\text{expression set of interest}]}} \cong 1$$

$\lambda$ denotes the clinical endpoints vector that indicates detectability thresholds for a specific DNA-hybridization array implementation $\kappa$ correspond to the uncertainty interval estimates.

An example of an equation selected for representing the VDC is:

$$\frac{\partial \rho}{\partial t} = \text{div}(\nabla \Psi(x)\rho) + \frac{\Delta \rho}{\beta}, \quad \rho(x, 0) = \rho^0(x)$$

The potential $\Psi(x): \Re^n \to [0, \infty)$ is a smooth function, $\beta > 0$ is selected constant, and $\rho^0(x)$ is a probability density on $\Re^n$.

Preferably, the diffusion potential of the equation and the BVL data are such that:

$$\Psi(x) < c[BVL_{NP\_LOW}, BVL_{LOW}]$$

the constant c is generally set to

Using the above expression, a conservative lower bound for interferometric enhancement is estimated for each nucleotide expression of interest. Since the array fabrication device is assumed to have (i) an identical o $$\dot{x} = \gamma \sin^k\left[\frac{\sqrt{\omega}}{\alpha}(\beta_0 + \beta_1 x + \beta_2 x^2)\right]\sin\omega t + \varepsilon(t)$$

with constants $\alpha$, $\beta$, $\gamma$ and $\epsilon \ll 1$.

This utility of this parameterization is established as follows. The VDC canonical representation is based on a variational formulation of the Fokker-Planck. The Fokker-Planck (FP) equation, or forward Kolmogorov equation, describes the evolution of the probability density for a stochastic process associated with an Ito stochastic differential equation. The exemplary method exploits the VDC to model a physical time-dependent phenomena in which randomness plays a major role. The specific variant used herein is one for which the drift term is given by the gradient of a potential. For a broad class of potentials (that correspond to statistical variability in therapy response), a time discrete, iterative variational is constructed whose solutions converge to the solution of the Fokker-Planck equation. The time-step is governed by the Wasserstein metric on probability measures. In this formulation the dynamics may be regarded as a gradient flux, or a steepest descent for the free energy with respect to the Wasserstein metric. This parameterization draws from theory of stochastic differential equations: wherein a (normalized) solution to a given Fokker-Planck equation represents the probability density for the position (or velocity) of a particle whose motion is described by a corresponding Ito stochastic differential equation (or Langevin equation). The drift coefficient is a gradient. The method exploits "designer conditions" on the drift and diffusion coefficients so that the stationary solution of a Fokker-Planck equation satisfies a variational principle. It minimizes a certain convex free energy functional over an appropriate admissible class of probability densities.

A physical analogy is to an optimal control problem which is related to the heating of a probe in a kiln. The goal is to control the heating process in such a way that the temperature inside the probe follows a certain desired temperature profile. The biomolecular analogy is to seek a certain property in the parameterized VDC—namely, an exponential jump in the VDC coordinate position for "small linear changes in the viral count".

This method is in contradistinction to conventional calibration strategies which obtain a linear or superlinear shift in quantization parameter for an exponential shift in actual viral count.

As noted, the form of FP equation chosen is $$\frac{\partial\rho}{\partial t} = div(\nabla\Psi(x)\rho) + \frac{\Delta\rho}{\beta}, \quad \rho(x, 0) = \rho^0(x)$$

where the potential $\Psi(x)$: $\mathfrak{R}^n \to [0, \infty)$ is a smooth function, $\beta > 0$ is selected constant, and $\rho^0(x)$ is a probability density on $\mathfrak{R}^n$. The solution $\rho(t,x)$ is a probability density on $\mathfrak{R}^n$ for almost every fixed time t. So the distribution $\rho(t,x) \geqq 0$ for almost every $(t,x) \in (0,\infty) \times \mathfrak{R}^n$, and $$\int_{\mathbb{R}^n} \rho(t, x)dx = 1$$

.for almost every t, $\in (0,\infty)$.

It is reasonably assumed that hybridization array device physics for the DNA biomicroarray (i.e., corresponding to the potential Ψ) has an approximately linear response to the nucleotide concentration and the response is monotonic with bounded drift. So, $$\rho_s(x) = \frac{1}{Z}e^{(-\beta\Psi(x))}$$

where the partition function Z is given by $$Z = \int_{\mathbb{R}^n} e^{(-\beta\Psi(x))}dx$$

In this model the basis for device physics design is that the potential needs to be modulated such that it grows rapidly enough for Z to be finite. This is not achieved by conventional methods. However, a technique which does achieve this result is described in co-pending U.S. patent application Ser. No. 09/253,789, now U.S. Pat. No. 6,136,541, filed contemporaneously herewith, entitled "Method and Apparatus for Analyzing Hybridized DNA Microarray Patterns Using Resonant Interactions Employing Quantum Expressor Functions", which is incorporated by reference herein.

The probability measure $\rho_s(x)dx$ is the unique invariant measure for the Markov random field (MRF) fit to the empirical viral load data.

The method exploits a special dynamical effect to design ρ. The method restricts the FP equation form above to a more restricted case: random walk emulating between critical equilibrium points.

To aid in understanding this aspect of the invention, consider the diffusion form $$\frac{\partial\rho(x, t)}{\partial t} = \frac{1}{2}D^2\frac{\partial^2\rho(x, t)}{\partial^2 t}$$

where $D^2 = \pi\alpha^2$ and α is constant.

A specific VDC shape is parameterized by:

$$y(x) = \beta_0 + \beta_1 x + \beta_2 x^2$$

subject to constraints $$\dot{x} = \gamma\sin^k\left[\frac{\sqrt{\omega}}{\alpha}(\beta_0 + \beta_1 x + \beta_2 x^2)\right]\sin\omega t + \varepsilon(t)$$

with constants α, β, γ and $\epsilon \ll 1$.

These constants are set based upon the dynamic range expected for the viral load. Thus, if the viral load is expected to vary only within a factor of 10, the constants are set accordingly. If the viral load is expected to vary within a greater range, different constants are employed. The actual values of the constants also depend upon the particular disease.

Where the following conditions are met
Expectation match:

$$E(x) = \int_{-\infty}^{\infty} xf(x)dx = \mu$$

Variance:

$$\sigma^2 = \int_{-\infty}^{\infty} (x-\mu)^2 f_x dx$$

And $$\int_{-\infty}^{\infty} f(x) = 1$$

The expectation and mean response parameters for use in these equations are derived, as described above, from matching the enhanced and normalized hybridization amplitude mean and variance that correspond to calibrated viral counts (via classical PCR amplification).

A distribution represented by the above-equations then satisfies the following form with a prescribed probability distribution $$\dot{x} = \gamma \sin^k\left[\frac{\sqrt{\omega}}{\alpha} y(x)\right] \sin\omega t + \varepsilon(t)$$

Assuming:

$$y' = \frac{dy}{dx} > \beta > 0, \quad \beta = \text{constant}$$

and $\epsilon(t) = \epsilon_0 ay$
such that $$\dot{a} = a^{1/3}(y-1)(y+1) - \epsilon_0 a$$

and the distribution controlling equation is $$f(x) = 0.5|y'(x)|$$

such that $y(-1) < X < y(1)$.

The characteristic timescale of response for this system is given by $$T^* = \frac{1}{\omega}\arccos\left[1 - \frac{B(1/3, 1/3)}{\sqrt[3]{2}} \frac{\alpha\sqrt{\omega}}{\gamma}\right]$$

the successive points must show a motion with characteristic timescale. The VDC is designed such that sampling time falls well within characteristic time.

As noted the actual information used for populating above the parameters is available from the following: Baseline viral load (BVL) set point measurements at which detection is achieved; BVL at which therapy is recommended; and VL markers at which dosage change recommended.

The following provides an example of preclinical data that is available to to assist in parameterizing the VDC.

Notional Viral Load Management Example

This is a synthetic example to illustrate how data from clinical studies may be used to calibrate the VDC.

Viral Load analysis studies, using conventional assays, in HIV progression have shown that neither gender, age, HCV co-infection, past history of symptomatic HIV-1 infection, duration of HIV-1 infection nor risk group are associated with a higher risk of increasing baseline viral load (BVL) to the virologic end-point. However, patients with a high (BVL) between 4000–6000 copies had a 10-fold higher risk of increasing the level of viral load than patients with a BVL below 1500 copies/ml. Thus, baseline viral load set point measurements provide an important indicator for onset of disease.

Initiation of antiretroviral therapy is generally recommended when the CD4+ T-cell count is <600 cells/mL and the viral load level is >6,000 copies/mL. When the viral load is >28000 copies/mL, initiation of therapy is recommended regardless of other laboratory markers and clinical status.

Effective antiretroviral treatment may be measured by changes in plasma HIV RNA levels. The ideal end point for effective antiviral therapy is to achieve undetectable levels of virus (<400 copies/mL). A decrease in HIV RNA levels of at least 0.5 log suggests effective treatment, while a return to pretreatment values (±0.5 log) suggests failure of drug treatment.

When HIV RNA levels decline initially but return to pretreatment levels, the loss of therapy effectiveness has been associated with the presence of drug-resistant HIV strains.

The therapy-specific preclinical viral load markers (such as low and high limits in the above example) are used to establish actual BVL boundaries for the VDC associated with a particular therapy. In this regard, the determination of the BVL parameters is disease specific. For example, in HIV methods such as RT-PCR, bDNA or NASBA are used. Other diseases use other assays. Typically, once the parameters of the VDC equation have been set (i.e. constants $\alpha$, $\beta$, $\gamma$ and $\epsilon$), only two viral load markers are needed to complete the parameterization of the VDC. This is in contrast to previous techniques whereby expensive and laborious techiques are required to determine the shape of a viral diffusion curve. The present invention succeeds in using only two viral load markers in most cases by exploiting the canonical VDC described above which has predefined properties and which is predetermined based upon the particular biochip being used.

Calibration of Viral Diffusion Curves

Referring again to FIG. 1, the directional causality of the VDC is calibrated at step 104 in the context of an NIF discussed in greater detail below. At least arbitrarily selected three sample points are used execute the NIF calibration computation. The resulting polynomial is used to extracting qualitative coherence properties of the system.

The spectral [ϴ]and temporal coherence [ϑ]is incrementally estimated and computed for each mutation/oligonucleotide of interest by a NIF forward estimation computation (described further below). The two estimates are normalized and convolved to yield cross-correlation function over time. The shape index (i.e., curvature) of the minima is used as a measure for directional causality. Absence of curvature divergence is used to detect high directional causality in the system.

Sample Collection

Samples are collected at step 106 subject to a sample point collection separation amount. The separation amount for two samples is preferably within half a "drug effectiveness mean time" covering 2σ population level wherein a denotes the standard deviation in period before which a effectiveness for a particular drug is indicated. The following are some general guidelines for sample preparation for use with the exemplary method:

It is important that assay specimen requirements be strictly followed to avoid degradation of viral RNA.

A baseline should be established for each patient with two specimens drawn two to four weeks apart.

Patients should be monitored periodically, every three to four months or more frequently if therapy is changed. A viral load level that remains at baseline or a rising level indicates a need for change in therapy.

Too much significance should not be given to any one viral load result. Only sustained increases or decreases of 0.001–0.01 log [conventional methods typically require a 0.3–0.5 log change] or more should be considered significant. Biological and technical variation of up to 0.01 log [typical conventional limit: 0.3 log] is possible. Also, recent immunization, opportunistic infections and other conditions may cause transient increases in viral load levels.

A new baseline for each patient should be established when changing laboratories or methods.

Recommendations for frequency of testing are as follows:
establish baseline: 2 measurements, 2 to 4 weeks apart
every 3 to 4 months or in conjunction with $CD4^+$ T-cell counts
3 to 4 weeks after initiating or changing antiretroviral therapy
shorter intervals as critical decisions are made.
measurements 2–3 weeks apart to determine a baseline measurement.
repeat every 3–6 months thereafter in conjunction with CD4 counts to monitor viral load and T-cell count.
avoid viral load measurements for 3–4 weeks following an immunization or within one month of an infection.
a new baseline for each patient should be established when changing laboratories or methods.

The samples are applied to a prefabricated DNA biomicroarray to generate one or more dot spectrograms each denoted $\Phi(i,j)$ for i: 1 to N, and j: 1 to M. The first sample is referred to herein as the k=1 sample, the second as the k=2 sample, and so on.

Interferometric Enhancement of the Dot Spectrogram

Each dot spectrogram provided by the DNA biomicroarray is filtered at step 108 to yield enhanced dot spectrograms $\Phi(\kappa)$ either by performing a conventional Nucleic Assay Amplification or by applying preconditioning and normalization steps as described in the co-pending patent application having Ser. No. 09/253,789, now U.S. Pat. No. 6,136,541, entitled "Method And Apparatus For Analyzing Hybridized Biochip Patterns Using Resonance Interactions Employing Quantum Expressor Functions". The application is incorporated by reference herein, particularly insofar as the descriptions of the use of preconditioning and normalization curves are concerned.

Fractal Filtering

Figure 3:
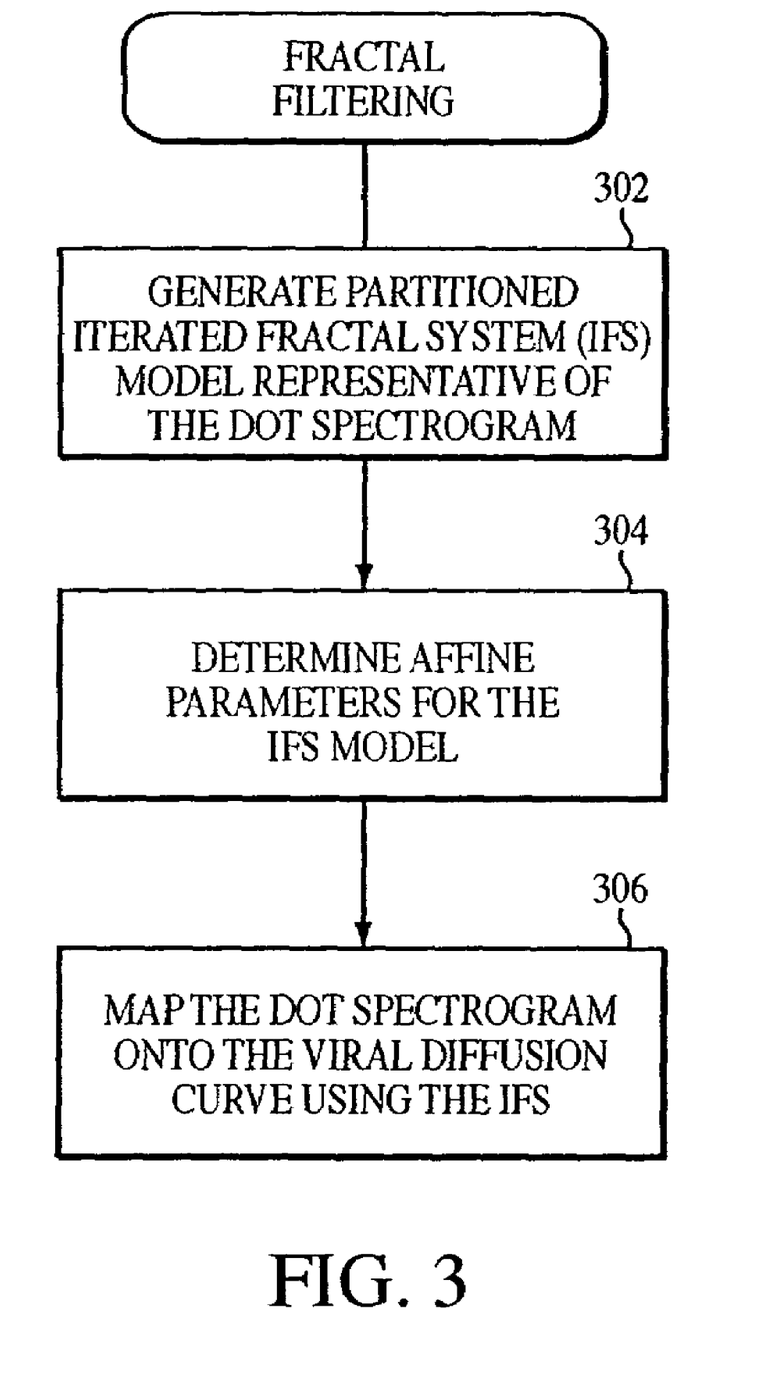
FIG. 3 is a flow chart illustrating an exemplary method for mapping dot spectrograms onto Viral Diffusion Curves using fractal filtering for use with the method of FIG. 1.

Each enhanced dot spectrogram is then mapped to the VDC using fractal filtering at step 110 as shown in FIG. 3 by generating a partitioned iterated fractal system 302, determining affine parameters for the IFS 304 and then mapping the enhanced dot spectrogram onto the VDC using the IFS, step 306.

The VDC representation models a stochastic process given by $$W(f)(x,y) = \begin{cases} \gamma_i \cdot f\left(\frac{1}{\sigma_i}\left(\frac{x-x_D^i}{y-y_D^i}\right) + \frac{x_R^i}{y_R^i}\right) + \tau\left(\frac{x-x_D^i}{y-y_D^i}\right) + \beta_i, \\ \quad \text{if } (x,y) \in \mu_i^{-1}(1), \text{ for some } 1 \le i \le m; \\ 0, \quad \text{otherwise;} \end{cases}$$

for any $(x,y) \in \Re^2$ and $f \in_\wp \Re^{i2}$)

An exemplary partitioned iterated fractal system (IFS) model for the system is $W = \{\Phi_i = (\mu_i, T_i)\} i=1, 2, \ldots, m$ where the affine parameters for the IFS transformation are given by $$T_i = \left((x_D^i, y_D^i), (x_R^i, y_R^i), \sigma_i = \begin{pmatrix} s_{00}^i & s_{01}^i \\ s_{10}^i & s_{11}^i \end{pmatrix}, \tau_i = (t_0^i, t_1^i), \gamma_i, \beta_i, \right)$$

where the D-origin is given by $(x_D^i, y_D^i)$,
the R-origin is given by $(x_R^i, y_R^i)$
spatial transformation matrix is given by $\rho_i$
the intensity tilting vector is given by $\tau_i$
the contrast adjustment is given by $\gamma_i$,
the brightness adjustment is given by $\beta_i$,
and wherein Φ represents the enhanced dot spectrogram and wherein μ represents the calculated expectation match values This IFS model maps the dot spectrogram to a point on the VDC wherein each VDC coordinate is denoted by VDC(t,Θ) such that $W[\Phi, k] \rightarrow VDC(k, \Theta)$ Wherein k represents a sample.

In the above equation, Θ represent the parameters of the IFS map.

Thus the output of step 110, is a set of VDC coordinates, identified as VDC(k, Θ), with one set of coordinates for each enhanced dot spectrogram k=1, 2 . . . n.

Figure 4:
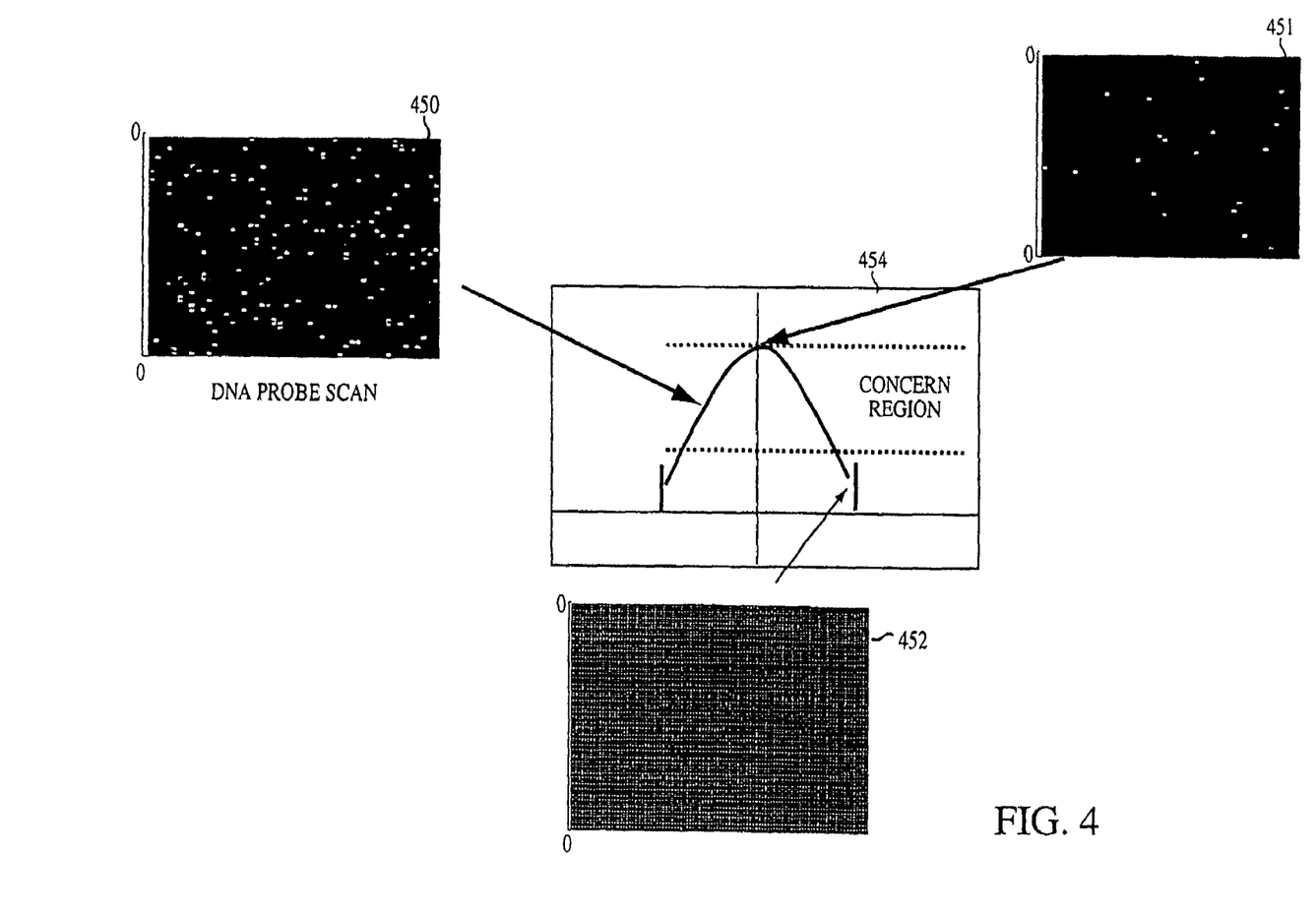
FIG. 4 is a block diagram illustrating the effect of the fractal filtering of FIG. 3.

The effect of the steps of FIG. 3 is illustrated in FIG. 4 which shows a set of dot spectrograms 450, 451 and 452 and a VDC 454. As illustrated, each dot spectrogram is mapped to a point on the VDC. Convergence toward a single point on the VDC implies ineffectiveness of the viral therapy. A convergence test is described below.

Uncertainty Compensation

Figure 5:
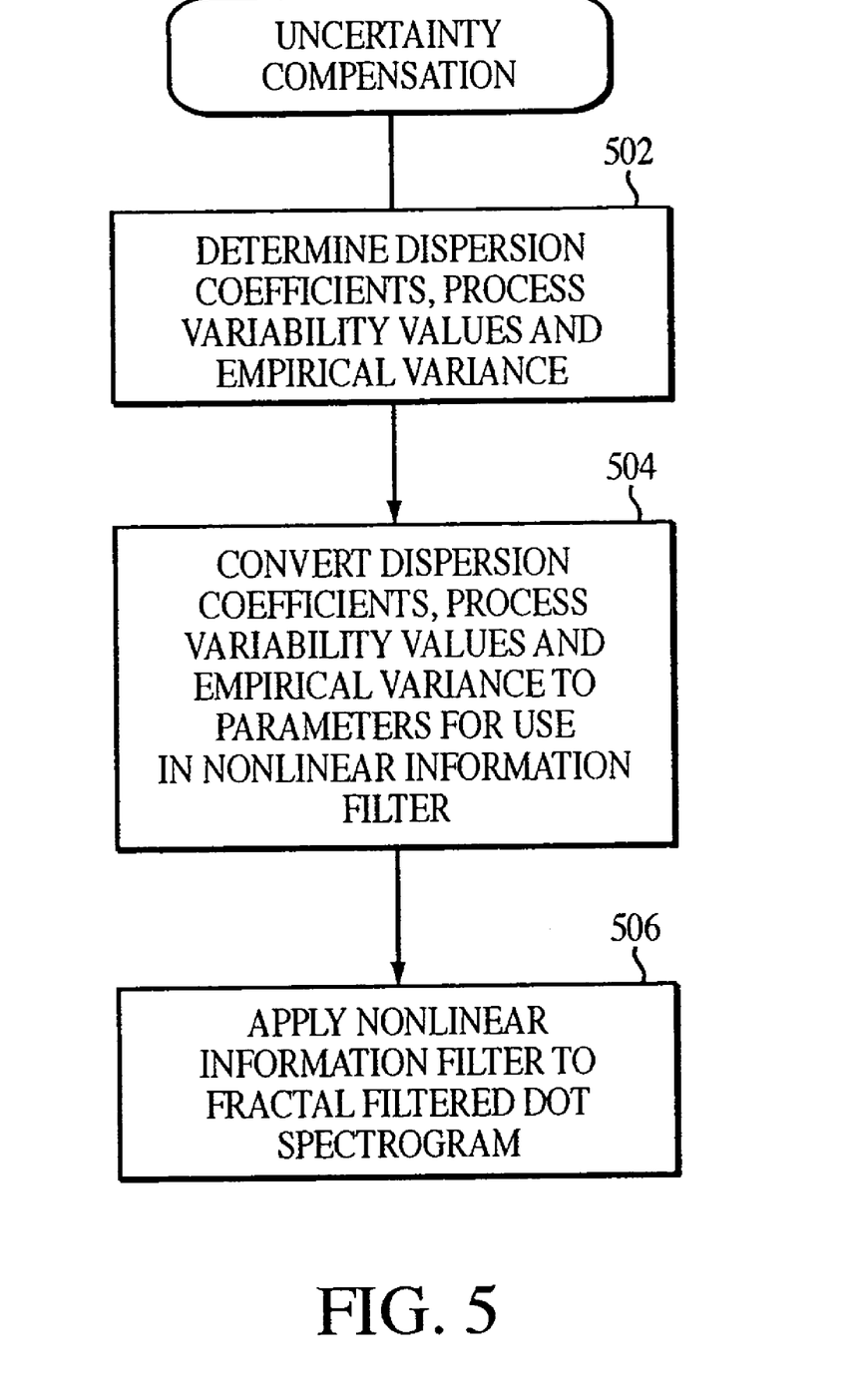
FIG. 5 is a flow chart illustrating an exemplary method for compensating for uncertainty using non-linear information filtering for use with the method of FIG. 1.

With reference to FIG. 5, any uncertainty in the coordinates VDC(k, Θ) is compensated using Non-linear Information Filtering as follows. Biomicroarray dispersion coefficients, hybridization process variability values and empirical variance are determined at step 402. The biomicroarray dispersion coefficients, hybridization process variability values and empirical variance are then converted at step 404 to parameters for use in NIF. The NIF is then applied at step 406 to the VDC coordinates generated at step 106 of FIG. 1.

Nonlinear information filter (NIF), is a nonlinear variant of the Extended Kalman Filter. A nonlinear system is considered. Linearizing the state and observation equations, a linear estimator which keeps track of total state estimates is provided. The linearized parameters and filter equations are expressed in information space. This gives a filter that predicts and estimates information about nonlinear state parameters given nonlinear observations and nonlinear system dynamics.

The information Filter (IF) is essentially a Kalman Filter expressed in terms of measures of the amount of about the parameter of interest instead of tracking the states themselves, i.e., track the inverse covariance form of the Kalman filter. Information here is in the Fisher sense, i.e. a measure of the amount of information about a parameter present in the observations.

Uncertainty bars are estimated using NIF algorithm. The parameters depend on biomicroarray dispersion coefficients, hybridization process variability and empirical variance indicated in the trial studies.

One particular advantage of the method of the invention is that it can also be used to capture the dispersion from individual to individual, therapy to therapy etc. It is extremely useful and enabling to the method in that it can be apriori analytically set to a prechosen value and can be used to control the quality of biomicroarray output mapping to VDC coordinates.

The biomicroarray dispersion coefficients, hybridization process variability values and empirical variance are determined as follows. Palm generator functions are used to capture stochastic variability in hybridization binding efficacy. This method draws upon results in stochastic integral geometry and geometric probability theory.

Geometric measures are constructed to estimate and bound the amplitude wanderings to facilitate detection. In particular we seek a measure for each mutation-recognizer centered (MRC-) hixel that is invariant to local degradation. Measure which can be expressed by multiple integrals of the form $$m(Z) = \int_Z f(z)dz$$

where Z denotes the set of mutations of interest. In other words, we determine the function f(z) under the condition that m(z) should be invariant with respect to all dispersions ξ. Also, up to a constant factor, this measure is the only one which is invariant under a group of motions in a plane. In principle, we derive deterministic analytical transformations on each MRC-hixel., that map error-elliptic dispersion bound defined on $\Re^2$ the two dimension Euclidean space—i.e., oxel layout) onto measures defined on $\Re^2$. The dispersion bound is given by $$\text{Log}_4(\hat{O}_{(i,j)}|^Z).$$

Such a representation of uniqueness facilitates the rapid decimation of the search space. It is implemented using a filter constructed using measure-theoretic arguments. The transformation under consideration has its theoretical basis in the Palm Distribution Theory for point processes in Euclidean spaces, as well as in a new treatment in the problem of probabilistic description of MRC-hixel dispersion generated by a geometrical processes. Latter is reduced to a calculation of intensities of point processes. Recall that a point process in some product space E×F is a collection of random realizations of that space represented as $\{(e_i, f_i), |e_i \in E, f_i \in F\}$.

The Palm distribution, Π of a translation $(T_n)$ invariant, finite intensity point process in $\Re^2$ is defined to the conditional distribution of the process. Its importance is rooted in the fact that it provides a complete probabilistic description of a geometrical process.

In the general form, the Palm distribution can be expressed in terms of a Lebesgue factorization of the form $$E_P N^* = \Lambda L_N \times \Pi$$

Where Π and Λ completely and uniquely determine the source distribution P of the translation invariant point process. Also, $E_P N^*$ denotes the first moment measure of the point process and $L_N$ is a probability measure.

Thus a determination of Π and Λ is needed which can uniquely encode the dispersion and amplitude wandering associated with the MRC-hixel. This is achieved by solving a set of equations involving Palm Distribution for each hybridization (i.e., mutation of interest). Each hybridization is treated as a manifestation of a stochastic point process in $\Re^2$.

In order to determine Π and Λ we have implemented the following measure-theoretic filter:

Determination of Λ
using integral formulae constructed using the marginal density functions for the point spread associated with MRC-hixel(i,j)

The oligonucleotide density per oxel $\rho_{m(i,j)}$, PCR amplification protocol $(\sigma_m)$, fluorescence binding efficiency $(\eta_m)$ and imaging performance $(\overline{\omega}_m)$ provide the continuous probability density function for amplitude wandering in the m-th MRC-hixel of interest. Let this distribution be given by $\wp(\rho_{m(i,j)}, \sigma_m, \eta_m, \overline{\omega}_m)$.

The method requires a preset binding dispersion limit to be provided to compute Λ. The $$\wp(\rho_{m(i,j)}, \sigma_m, \eta_m, \overline{\omega}_m)$$

second moment to the function
at SNR=0 condition is used to provide the bound.
Determination of Π
Obtained by solving the inverse problem $$\Pi = \Theta * P$$

where $$P = \int_{\tau_1}^{\tau_2} \wp(\rho_{m(i,j)}, \sigma_m, \eta_m, \overline{\omega}_m) \partial\tau$$

where $\tau_1$ and $\tau_2$ represent the normalized hybridization dispersion limits.

The number are empirically plugged in. The values of 0.1 and 0.7 are appropriate for, respectively, signifying loss of 10%–70% hybridization. Also, Θ denotes the distribution of known point process. The form $1/(1+\exp(\wp(\ldots)))$ is employed herein to represent Θ.

The biomicroarray dispersion coefficients, hybridization process variability values and empirical variance are then converted to parameters at step 304 for use in NIF as follows.

The NIF is represented by:

Predicted State=f(current state, observation model, information uncertainty, information model)

Detailed equations are given below.

In the biomicroarray context, NIF is an information-theoretic filter that predicts and estimates information about nonlinear state parameters (quality of observable) given nonlinear observations (e.g., post hybridization imaging)

and nonlinear system dynamics (spatio-temporal hybridization degradation). The NIF is expressed in terms of measures of the amount of information about the observable (i.e., parameter of interest) instead of tracking the states themselves. It has been defined as the inverse covariance of the Kalman filter, where the information is in the Fisher sense, i.e, a measure of the amount of information about $o_I$ present in the observations $Z^k$ where the Fisher information matrix is the covariance of the score function.

In a classical sense the biomicroarray output samples can be described by the nonlinear discrete-time state transition equation of the form:

$$VDC(k)=f(VDC(k-1),\Phi(k-1), k)+v(k)$$

where VDC(k-1) is the state at time instant (k-1), $\Phi$(k-1) is the input vector (embodied by dosage and/or therapy)

v(k) is some additive noise; corresponds to the biomicroarray dispersion as computed by the Palm Generator functions above.

VDC(k) is the state at time k, f(k,.,.) is the nonlinear state transition function mapping previous state and current input to the current state. In this case it is the fractal mapping that provides the VDC coordinate at time k.

The observations of the state of the system are made according to a non-linear observation equation of the form $$z(k)=h(VDC(k))+w(k)$$

where z(k) is the observation made at time k

VDC(k) is the state at time k, w(k) is some additive observation noise and h(.,k) is the current non-linear observation model mapping current state to observations, i.e., sequence-by-hybridization made at time k, v(k) and w(k) are temporally uncorrelated and zero-mean. This is true for the biomicroarray in how protocol uncertainties, binding dynamics and hybridization degradation are unrelated and additive. The process and observation noises are uncorrelated.

$$E[v(i)w^T(j)]=0,\ \forall i,j.$$

The dispersion coefficients together define the nonlinear observation model.

The nonlinear information prediction equation is given by $$\hat{y}(k|k-1)=Y(k|k-1)f(k,\hat{VDC}(k-1|k-1),u(k-1))$$

$$Y(k|k-1)=[\nabla f_x(k)Y^{-1}(k-1|k-1)\nabla f_x^T(k)+Q(k)]^{-1}$$

The nonlinear estimation equations are given by $$\hat{y}(k|k)=\hat{y}(k|k-1)+i(k)$$

$$Y(k|k)=Y(k|k-1)+I(k)$$

where $$I(k)=\nabla h_x^T(k)R^{-1}(k)\nabla h_x(k)$$

$$i(k)=\nabla h_x^T(k)R^{-1}(k)[v(k)+\nabla h_x(k)\hat{VDC}(k|k-1)]$$

where $$v(k)=z(k)-h(\hat{x}(k|k-1)).$$

In this method NIF helps to bind the variability in the VDC coordinate mapping across sample to sample so that dosage and therapy effectiveness can be accurately tracked.

The NIF is then applied to enhanced, fractal-filtered dot spectrogram at step 306 as follows. States being tracked correspond to post-hybridization dot spectrogram in this method. NIF computation as described above specifies the order interval estimate associated with a VDC point. It will explain and bound the variability in Viral load estimations for the same patient from laboratory to laboratory.

The NIF also specifies how accurate each VDC coordinate is given the observation model and nucleotide set being analyzed.

Convergence Testing

Referring again to FIG. 1, once any uncertainty is compensated, the VDC coordinates are renormalized at step 114. The renormalized VDC coordinates are patient specific and therapy specific. Alternately the coordinates could be virus/nucleotide marker specific. The NIF-compensated VDC coordinates are renormalized to the first diagnostic sample point obtained using the biomicroarray. Thus a patient can be referenced to any point on the VDC.

This renormalization step ensures that VDC properties are maintained, notwithstanding information uncertainties as indicated by the NIF correction terms. The approach is drawn from "renormalization-group" approach used for dealing with problems with many scales. In general the purpose of renormalization is to eliminate an energy scale, length scale or any other term that could produce an effective interaction with arbitrary coupling constants. The strategy is to tackle the problem in steps, one step for every length scale. In this method the renormalization methodology is abstracted and applied during a posteriori regularization to incorporate information uncertainty and sample-to-sample variations.

This is in contradistinction to current viral load measurement calibration methods that either generate samples with same protocol and same assumptions of uncertainty or use some constant correction term. Both existing approaches skew the viral load readout so that measurements are actually accurate only in a limited "information" and "observability" context. This explains the large variations in readings from different laboratories and technicians for the same patient sample.

Specifically, we include the dynamic NIF correction function to the gradient of the VDC at the sample point normalized in a manner such that when the information uncertainty is null, the correction term vanishes. As discussed in the above steps, the NIF correction terms is actually derived from the noise statistics of the microarray sample.

$$<VDC(k,\Theta)>=VDC(k,\Theta)+[\nabla NIF(Y,I)_k]$$

where $\nabla NIF(Y,I)_k$ denotes the gradient of nonlinear information prediction function. Under perfect observation model this term vanishes.

Once initialized, the VDC coordinates are then updated at step 116 applying the IFS filter W[] on k+1th sample, by $$VDC(k+1,\Theta) \leftarrow W[\text{Biomicroarray Output}, K+1];$$

A direction convergence test is next performed at step 118 to determine whether the selected therapy has been effective. If convergence establishes that the viral load for the patient is moving in a direction representative of a lower viral load, then the therapy is deemed effective. The system is deemed to be converging toward a lower viral load if and only if:

$$\left\|\frac{VDC(t_k)-VDC(t_{k-j})}{VDC(t_{k-1})-VDC(t_{k-j})}\right\| > 1 \wedge \left\|\frac{VDC_{peak}-VDC(t_k)}{VDC_{peak}-VDC(t_{k-1})}\right\| < 1$$

-continued for $k > 2$ and $j > 0$

The above relationships needs to be monotonically persistent for at least two combinations of k and j.

Also, date[k]−date[j]<κ*characteristic time, f(in days)

Where κ captures the population variability. Typically, κ<1.2.

The peak VDC value is determined based on the VDC. The peak amplitude is an artifact of the specific parameterization to the Fokker-Planck equation used in deriving the VDC. It is almost always derived independent of the specific sample.

In connection with step 118, a VDC Shift factor Δ may be specified at which a dosage effectiveness decision and/or disease progression decision can be made. The VDC shift factor is applied to estimate the VDC curvature traversed between two measurements.

If the system is deemed to be converging toward a lower viral load, an output signal is generated indicating that the therapy of interest is effective at step 120. If not, then the execution proceeds to step 122 wherein VDC scale matching is performed. A key assumption underlying this method is that movement along VDC is significant if and only if the sample points are with a constant multiple of temporal scale characterizing the VDC. This does not in any way preclude the pharmacological relevance associated with the datapoints. But complete pharmacological interpretation of the sample points is outside the scope of this method. The process is assumed to be cyclostationary or at a large time scale and two or more sample points have been mapped to VDC coordinates. The coordinates are then plugged into an analytic to estimate the empirical cycle time ($\hat{t}$). This is implemented as described in the following sections.

Again the empirical cycle time ($\hat{t}$) is used to establish decision convergence.

Scale Matching

Select a forcing function of the form:

$$\Psi = k \cdot \wp^m \cos \omega t$$

where k is a constant and m is a small odd integer (m<7).

The phase space for this dynamical system is represented by:

$$\dot{x} = \gamma \sin\left[\frac{\sqrt{\omega}}{\alpha} \text{erf } m\left(\frac{x}{\sigma\sqrt{2}}\right)\right]^{\frac{k}{k+2}} \sin \omega t$$

where $$\text{erf } m(x) = \begin{cases} -1 & \text{if } x < -N \\ \text{erf}(x) & \text{if } |x| \le N \\ 1 & x > N \end{cases}$$

and erf m(.) denotes the error function.

K is set to 1; where o<α, γ, ω<1 are refer to constants.

Let $\tau_{emp}$ denote the cycle-time-scale for this empirical system.

If $\log_e(\tau_{emp}/T)>1$ (in step 10) then we claim that timescales do not match.

Time Scale Testing

Next a determination has been made as to whether an effectiveness timescale has been exceeded at step 124 by:

Checking if a time step between successive sampling has exceeded T by determining if $\text{Time}_{k+1} - \text{Time}_k > T$ such that VDC(k+1, Θ)−VDC(k, Θ))<ζ where
is set to 0.0001 and wherein
T is given by $$T^* = \frac{1}{\omega} \arccos\left[1 - \frac{B(1/3, 1/3)}{\sqrt[3]{2}} \frac{\alpha\sqrt{\omega}}{\gamma}\right]$$

B(1/3,1/3) represents the Beta function around the coordinates (1/3,1/3), We can actually use all B(1/2i+1,1/2i+1) for i>1 and i<7.

If $\text{Time}_{k+1} - \text{Time}_k > T$ then output signal at step 126 indicating that either
no change in viral load concluded, OR
therapy deemed ineffective, OR
dosage deemed suboptimal.

If $\text{Time}_{k+1} - \text{Time}_k < T$ then process another sample by repeating all steps beginning with Step 4 wherein a dot spectrogram is generated for a new sample.

If the effectiveness time scale has been exceeded then a signal is output indicating that no determination can be as to whether the therapy of interest is effective. If the time scale is not exceeded, then execution returns to step 106 for processing another sample. If available, and the processing steps are repeated.

Alternative Implementations

Details regarding a related implementation may be found in U.S. patent application Ser. No. 09/253,792, now U.S. Pat. No. 6,142,681, filed contemporaneously herewith, entitled "Method and Apparatus for Interpreting Hybridized Bioelectronic DNA Microarray Patterns Using Self Scaling Convergent Reverberant Dynamics", and incorporated by reference herein.

The exemplary embodiments have been primarily described with reference to flow charts illustrating pertinent features of the embodiments. Each method step also represents a hardware or software component for performing the corresponding step. These components are also referred to herein as a "means for" performing the step. It should be appreciated that not all components of a complete implementation of a practical system are necessarily illustrated or described in detail. Rather, only those components necessary for a thorough understanding of the invention have been illustrated and described in detail. Actual implementations may contain more components or, depending upon the implementation, may contain fewer components.

The description of the exemplary embodiments is provided to enable any person skilled in the art to make or use the present invention. Various modifications to these embodiments will be readily apparent to those skilled in the art and the generic principles defined herein may be applied to other embodiments without the use of the inventive faculty. Thus, the invention is not intended to be limited to the embodiments shown herein but is to be accorded the widest scope consistent with the principles and novel features disclosed herein.

What is claimed is:

1. A system for determining the level of a biological indicator within a patient sample applied to an array, where material associated with the array includes emitters emitting data indicative of the biological indicator, based on digitized output patterns from the array, comprising:

a preconditioning unit that modifies the digitized output pattern so that a scale of the digitized output pattern is compatible with a scale of a reference wave adapted for the array;

an interferometric unit configured to generate a plurality of resonances between the pre-conditioned digitized output pattern and the reference wave to enhance the digitized output pattern, the resonances identifying data indicative of the biological indicator within the patient sample; and an analysis unit for analyzing the interferometrically enhanced digitized output pattern to determine the level of the biological indicator.

2. A system for determining the level of specific constituents within an output pattern generated from a detected image of a biological sample applied to an array wherein the output pattern comprises signals associated with noise, and signals associated with the biological sample which have intensities both greater and less than intensities of signals associated with noise, comprising:

a processor to tessellate the output pattern to facilitate signal processing;

interferometric signal processing means for amplifying signals associated with the biological sample within the tessellated output pattern, having an intensity lower than the intensity of signals associated with noise, to an intensity greater than the intensity of the signals associated with noise to generate a modified output pattern;

first determination means for determining which signals within the modified output pattern correlate with specific constituents within the biological sample;

second determination means for determining specific constituents within the biological sample based on the signals within the modified output pattern correlating to specific constituents within the biological sample; and third determination means for associating the signals correlating to specific constituents with levels of such specific constituents within the sample.

3. A system for quantitating specific constituents within an output pattern generated from a detected image of a biological sample applied to an array wherein the output pattern comprises signals associated with noise, and signals associated with the biological sample which have intensities both greater and less than intensities of signals associated with noise, comprising:

a tessellation unit for segmenting the output pattern;

an interferometric signal processing unit to amplify signals associated with the biological sample within the segmented output pattern, having an intensity lower than the intensity of signals associated with noise, to an intensity greater than the intensity of the signals associated with noise to generate a modified output pattern;

a first determination unit to determine which signals within the modified output pattern correlate with specific constituents within the biological sample;

a second determination unit to determine specific constituents within the biological sample based on the signals within the modified output pattern correlating to specific constituents within the biological sample; and a mapping unit to map the signals correlating to specific constituents on a reference scale to determine the level of such specific constituents within the biological sample.

4. A method analyzing an output pattern of a biological sample applied to an array to determine the presence and quantity of specific constituents within a biological sample applied to the array, wherein the output pattern comprises signals associated with noise, and signals correlating to the biological sample with the signals correlating to the biological sample having intensities both greater and less than the signals associated with noise, the method comprising:

segmenting the output pattern of the array using tessellation;

interferometrically enhancing the segmented output pattern to amplify signals associated with the biological sample, having an intensity lower than the intensity of signals associated with noise, to an intensity greater than the intensity of the signals associated with noise to generate a modified output pattern;

associating signals within the interferometrically enhanced segmented output pattern with specific constituents within the biological sample;

determining specific constituents within the biological sample based on the signals within the interferometrically enhanced segmented output pattern associated with specific constituents within the biological sample; and mapping the signals associated with specific constituents to a reference scale.

5. A computer code product, embodied on computer readable media, that determines the presence of specific constituents within an output pattern of a biological sample applied to an array of detectors, wherein the output pattern comprises signals associated with noise, and signals associated with the biological sample which have intensities both greater and less than intensities of signals associated with noise, the computer code product comprising:

computer code that segments the output pattern using tessellation;

computer code that utilizes interferometric signal processing to amplify signals within the segmented output pattern associated with the biological sample having an intensity lower than the intensity of the signals associated with noise, to an intensity greater than the intensity of the signals associated with noise to generate a modified output pattern;

computer code that determines which signals within the modified output pattern correlate with specific constituents within the biological sample;

computer code tat determines specific constituents within the biological sample based on the signals within the modified output pattern correlating to specific constituents within the biological sample; and computer code that maps signals correlating to specific constituents to a reference scale.

6. A method for determining the level of a biological indicator within a patient sample applied to an arrayed information structure, where material associated with the arrayed information structure emits data indicative of the biological indicator, based on digitized output patterns from the arrayed information structure, comprising:

pre-conditioning the digitized output pattern so that it has a scale compatible wit a scale of a reference wave;

generating an interference by inducing resonances between the pre-conditioned digitized output pattern and the reference wave adapted for the arrayed information structure to enhance the digitized output pattern, the resonances identifying data indicative of the biological indicator within the patient sample; and analyzing the interferometrically enhanced digitized output pattern to determine the level of the biological indicator.

7. The method of claim 6, wherein the analyzing comprises:

generating a viral diffusion curve with a biological indicator of interest;

mapping the output patterns to the viral diffusion curve; and determining the degree of convergence between the mapped coordinates of the respective output patterns mapped on the viral diffusion curve.

8. The method of claim 6 wherein the generating an interference utilizes at least one of the group comprising: resonance interferometry, quantum resonance interferometry, and stochastic resonance interferometry.

9. The method of claim 6 further comprising the output pattern.

10. The method of claim 7 further coimprising performing nucleic acid amplification to enhance the output patterns prior to the mapping.

11. The method of claim 7 wherein the sample is selected from a group consisting of DNA, RNA, protein, peptide-nucleic acid (PNA) and targeted nucleic acid (TNA) samples.

12. The method of claim 6 wherein the pre-conditioning comprises tessellating the enhanced output pattern.

13. The system of claim 1, further comprising means for mapping the data indicative of the biological indicator to a viral diffusion curve.

14. The system of claim 1, further comprising means for determining viral load.

15. The system of claim 2, wherein the third determination means comprises means for mapping the signals correlating to specific constituents to a referencd scale.

16. The system of claim 15, wherein the specific constituents are associated with viral load and the reference scale is a viral diffusion curve.

17. The system of claim 2, wherein the signal processing means comprises resonance interferometry.

18. The system of claim 17, wherein the resonance interferometry comprises quantum resonance interferometry or stochastic resosance interferometry.

19. A system as in claim 1, wherein the reference wave is based on a quantum expressor function.

* * * * *